United States Patent [19]
Deucker et al.

[11] 3,954,810

[45] May 4, 1976

[54] PROCESS FOR THE PREPARATION OF 4-BROMONAPHTHALIC ACID ANHYDRIDE

[75] Inventors: Walter Deucker, Neuenhain, Taunus; Helmut Tröster, Frankfurt am Main, both of Germany

[73] Assignee: Hoechst Aktiengesellschaft, Frankfurt am Main, Germany

[22] Filed: Jan. 16, 1974

[21] Appl. No.: 433,795

[52] U.S. Cl............................ 260/345.2; 260/515 A
[51] Int. Cl.$^2$......................................... C07D 311/02
[58] Field of Search..................... 260/345.2, 515 A

[56] References Cited
UNITED STATES PATENTS

| | | | |
|---|---|---|---|
| 2,211,465 | 8/1940 | Jewel et al. | 260/515 A |
| 2,394,268 | 2/1946 | Spencer | 260/515 A |
| 3,163,659 | 12/1964 | Sieber | 260/615 A |

FOREIGN PATENTS OR APPLICATIONS

| | | | |
|---|---|---|---|
| 1,224,418 | 3/1971 | United Kingdom | 260/345.2 |

OTHER PUBLICATIONS

Petrenko et al., Chem. Abst., 68, (1968).

Carpignano, Chem. Abst., 51 (1957).

*Primary Examiner*—Howard T. Mars
*Attorney, Agent, or Firm*—Curtis, Morris & Safford

[57] ABSTRACT

A process for the preparation of 4-bromo-naphthalic acid anhydride by bromination of an alkali metal salt of naphthalic acid in an aqueous medium at a pH of 6.8 to 9 by dropwise adding 0.55 to 0.65 mol of bromine per mol of naphthalic acid and oxidizing the bromine at the same pH-value with chlorine. By this process 4-bromo-naphthalic acid anhydride can be obtained in a quantitative yield whereby the formation of 4-chloro-naphthalic acid is avoided.

6 Claims, No Drawings

PROCESS FOR THE PREPARATION OF 4-BROMONAPHTHALIC ACID ANHYDRIDE

The present invention relates to an improved process for the preparation of 4-bromo-naphthalic acid anhydride.

The preparation of 4-bromo-naphthalic acid anhydride by a portionwise addition of elementary bromine and sodium hydroxide solution to an aqueous solution of an alkali metal salt of naphthalic acid has been disclosed in U.S. Pat. No. 2,394,268. According to that process, about 1 mol of bromine is used per 1 mol of naphthalic acid anhydride. The 4-bromo-naphthalic acid anhydride obtained, however, still contains about 20 % of non-brominated starting material.

The disadvantage of that and other related methods for the preparation of 4-bromo-naphthalic acid anhydride is the high amount of expensive bromine required, of which less than 50 % is exploited for the bromination reaction. Therefore, the bromine has then to be recovered by oxidation from the mother- and washing liquors by subsequent additional operations. To overcome this difficulty, attempts have been made to reduce the amount of bromine required by simultaneously introducing chlorine for the oxidation of the resulting bromide ions. It is, however, known from U.S. Pat. No. 2,394,268 that, in a weakly alkaline medium required for the bromination of naphthalic acid, the presence of chlorine or hypochlorite, in addition to bromine, leads to unseparable mixtures of 4-chloro- and 4-bromo-naphthalic acid anhydrides.

It has now been found that an alkali metal salt of naphthalic acid can be monobrominated in an aqueous medium at a pH of 6.8 to 9 by dropwise adding 0.55 to 0.65 mol of bromine per mol of naphthalic acid and then introducing chlorine at the same pH-value.

According to the process of the invention, 0.55 to 0.65 mol of bromine per mol of naphthalic acid used is added dropwise to an aqueous solution of the sodium salt of naphthalic acid at a pH-value of 6.8 to 9.0, preferably of 7.2 to 8.5. Subsequently, chlorine gas is fed in until the degree of bromination required has been reached. The necessary neutral to weakly alkaline pH-value is maintained over the whole reaction period by evenly adding sodium hydroxide solution. For an amount of 0.55 to 0.65 mol of bromine, about 1 mol of chlorine is required in order to brominate entirely 1 mol of naphthalic acid so as to yield 4-bromo-naphthalic acid. Under the indicated conditions, the chlorine which has been fed in preferably reacts with the bromide ions present instead of reacting with the naphthalic acid in a chlorination reaction. The chlorine content of the 4-bromo-naphthalic acid anhydride so obtained is below 0.3 % and the content of starting material is less than 1 %.

The reaction is carried out at temperatures of 0° to 30°C, preferably of 10° to 25°C.

The optimum pH-range for the process is limited, toward the acidic side, by the stability of the di(alkali metal) salts of the naphthalic acid and, toward the alkaline side, it is limited at about 9 by an increasing number of side reactions, such as the formation of bromate and chlorate.

To dissolve the naphthalic acid anhydride and to maintain the necessary pH-value during the bromination reaction, potassium hydroxide solution, sodium carbonate and potassium carbonate or mixtures of the said products may also be used in addition to sodium hydroxide solution.

Instead of using chlorine gas in the presence of an alkaline agent, it is also possible to feed in a sodium or potassium hypochlorite solution for the oxidation of the resulting bromide, all the other conditions being the same. In this case, the pH-value is maintained by a simultaneous addition of an acid, for example hydrochloric acid or acetic acid.

When the chlorination reaction is complete, the mixture is worked up according to known methods. After clarification by filtration, where required, the solution may be acidified with a mineral acid at room temperature or at a temperature of up to about 90°C, the bromination product which has precipitated may be separated, washed with water and dried at 100°–120°C. An especially pure product is obtained by salting out the resulting 4-bromo-naphthalic acid in the form of the disodium salt by an addition of sodium ions to the reaction solution, for example in the form of sodium chloride and/or sodium hydroxide, separating the salt and converting it into the anhydride by introducing it into a dilute mineral acid. The 4-bromo-naphthalic acid anhydride so obtained is a valuable intermediate product for the preparation of dyestuffs and optical brighteners of the series of the naphthalic acid derivatives substituted in 4-position by phenols, thiophenols and aromatic amines.

The following Examples serve to illustrate the invention.

EXAMPLE 1

100 Grams of naphthalic acid anhydride were dissolved at 60°C in 1600 ml of water and 150 g of a 33 % sodium hydroxide solution. At 15°–20°C, the pH-value was adjusted to 7.3 – 7.6 by means of phosphoric acid and 45 g of bromine were added dropwise. To maintain the pH-value, a 10 % sodium hydroxide solution was simultaneously added dropwise. Subsequently, about 35 g of chlorine gas were fed into the mixture over 1 hour so that a total amount of 445 g of a 10 % sodium hydroxide solution was consumed for maintaining the pH-value from the beginning of the bromination reaction. Stirring was continued for 1 to 2 hours. Upon clarification by filtration the filtrate was heated to 70° – 80°C and acidified by means of hydrochloric acid, and the precipitate was suction-filtered, washed with water and dried at 100° to 120°C. Yield: 109 g.

Bromine content: calculated 28.9 %, found 29.2 %. Chlorine content: below 0.3 %.

EXAMPLE 2

100 Grams of naphthalic acid were brominated as in Example 1. After clarification by filtration, 100 g of a 33 % sodium hydroxide solution and 400 g of sodium chloride were added to the filtrate and after 3 hours the precipitate was rapidly suction-filtered, washed out twice with a saturated sodium chloride solution and suspended in 1200 ml of water. The suspension was acidified at 70°C with hydrochloric acid, heating was continued for 2 hours, and the anhydride was suction-filtered, washed until neutral and dried. Yield: 99 grams. Content of pure product: above 99 % (established by gas chromatography), chlorine content: below 0.3 %.

EXAMPLE 3

100 Grams of naphthalic acid anhydride were dissolved as in Example 1 and the solution was reacted with 45 g of bromine at pH 7.3 – 7.6 and at a temperature of 15° to 20°C. To complete the bromination reaction 275 g of a 12.8 % sodium hypochlorite solution were then added dropwise and to maintain the pH-value 124 g of a 10 % hydrochloric acid were added dropwise. The 4-bromo-naphthalic acid anhydride was isolated as in Example 1. Yield: 108 grams. Content of pure product: above 97 % (established by gas chromatography). Chlorine content: below 0.3 %.

EXAMPLE 4

100 Grams of naphthalic acid anhydride were dissolved in 1600 ml of water and 154 g of a 45 % potassium hydroxide solution. At 15°–20°C, a pH-value of 8.0 – 8.5 was adjusted by means of acetic acid and 48 g of bromine were added dropwise. To maintain the pH-value a 15 % potassium hydroxide solution as added dropwise at the same time. Subsequently, about 35 g of chlorine gas were fed into the mixture so that a total amount of 432 g of a 15 % potassium hydroxide solution was consumed for maintaining the pH-value from the beginning of the bromination reaction. Stirring was continued for 1 to 2 hours and the product was worked up as in Example 1. Yield: 109 grams. Content of pure product: 98 % (gas chromatography). Chlorine content: below 0.3 %.

We claim:

1. In a process for preparing 4-bromo-naphthalic acid anhydride by reacting bromine with naphthalic acid in aqueous solution and isolating the product by acidifying the reaction mixture, the improvement which comprises gradually adding bromine to an aqueous solution of an alkali metal salt of naphthalic acid while maintaining the pH of said solution between 6.8 and 9 and while maintaining the temperature of said solution between 0° and 30°C., 0.55 to 0.65 mol of bromine being added per mol of naphthalic acid, and thereafter adding to said solution either about one mol of chlorine gas or an equivalent amount of a solution of sodium or potassium hypochlorite per mol of naphthalic acid until the degree of bromination required has been reached and while maintaining said pH and temperature, whereby a product having a chlorine content below 0.3 percent is obtained.

2. A process improvement according to claim 1 wherein said pH is maintained at between 7.2 and 8.5.

3. A process improvement according to claim 1 wherein said temperature is maintained at between 10° and 25°C.

4. A process improvement according to claim 1 wherein chlorine gas is added to said solution.

5. A process improvement according to claim 1 wherein said hypochlorite is added to said solution.

6. A process improvement according to claim 5 wherein said pH is maintained during addition of said hypochlorite by adding hydrochloric acid or acetic acid to said solution.

* * * * *

UNITED STATES PATENT AND TRADEMARK OFFICE
CERTIFICATE OF CORRECTION

PATENT NO. : 3,954,810
DATED : May 4, 1976
INVENTOR(S) : Deucker et al.

It is certified that error appears in the above-identified patent and that said Letters Patent are hereby corrected as shown below:

In the Heading, under Item [21] insert:

--[30] Foreign Application Priority Data

January 18, 1973        Germany        23 02 372--.

*Signed and Sealed this*

*Thirteenth Day of July 1976*

[SEAL]

*Attest:*

RUTH C. MASON
*Attesting Officer*

C. MARSHALL DANN
*Commissioner of Patents and Trademarks*